United States Patent [19]
Van Atta

[11] Patent Number: 5,632,877
[45] Date of Patent: May 27, 1997

[54] RAPID ASSEMBLY ELECTROPHORESIS CELL FOR SLAB GELS

[75] Inventor: Daniel L. Van Atta, Clayton, Calif.

[73] Assignee: Bio-Rad Laboratories, Inc., Hercules, Calif.

[21] Appl. No.: 650,388

[22] Filed: May 20, 1996

[51] Int. Cl.⁶ .................. G01N 27/26; G01N 27/447
[52] U.S. Cl. ................ 204/618; 204/467; 204/616
[58] Field of Search .................... 204/456, 457, 204/458, 459, 461, 462, 463, 464, 465, 466, 467, 468, 469, 470, 606, 607, 608, 609, 610, 612, 613, 614, 615, 616, 617, 618, 619, 620, 621

[56] References Cited

U.S. PATENT DOCUMENTS

| | | | |
|---|---|---|---|
| 3,856,655 | 12/1974 | Roberts | 204/618 |
| 4,142,960 | 3/1979 | Hahn et al. | 204/619 |
| 4,292,161 | 9/1981 | Hoefer et al. | 204/618 |
| 4,339,327 | 7/1982 | Tyler | 204/619 |
| 4,518,476 | 5/1985 | Delony et al. | 204/618 |
| 4,574,040 | 3/1986 | Delony et al. | 204/606 |
| 4,732,657 | 3/1988 | November et al. | 204/618 |
| 4,773,984 | 9/1988 | Flesher et al. | 204/618 |
| 4,865,715 | 9/1989 | Hellman, Jr. | 204/618 |
| 4,929,329 | 5/1990 | Danby et al. | 204/608 |
| 5,112,470 | 5/1992 | Sylvester | 204/618 |

*Primary Examiner*—Kathryn L. Gorgos
*Assistant Examiner*—John S. Starsiak, Jr.
*Attorney, Agent, or Firm*—Townsend and Townsend and Crew LLP

[57] ABSTRACT

Slab gels in parallel plate gel enclosures are readily placed in an electrophoresis cell where they are in full contact with upper and lower electrode buffers and reliably sealed against leakage with relatively few manual manipulations. The gel enclosures are pressed against an inner frame to form an upper buffer chamber, and the inner frame is inserted in an outer clamping frame in which the pressure between the gel enclosures and the inner frame is maintained by a cam-operated pressure plate. The clamping frame is then placed in a tank serving as the lower buffer chamber.

10 Claims, 6 Drawing Sheets

RAPID ASSEMBLY ELECTROPHORESIS CELL FOR SLAB GELS

This invention relates to electrophoresis cells for slab gel electrophoresis.

BACKGROUND OF THE INVENTION

Slab gel electrophoresis is widely used for separating mixtures of chemical species, particularly complex species such as proteins, polypeptides, nucleic acids and oligonucleotides. Slab gels offer the advantage of allowing multiple samples to be analyzed simultaneously, and using the gels in a vertical orientation is beneficial for inserting samples in wells formed along the top edge, and for achieving fluid contact of the top and bottom edges of the gels with separate buffer solutions for the top and bottom electrodes respectively.

The need to keep the two buffer solutions separate from each other while achieving full liquid contact along both top and bottom edges of the gels has required complex apparatus and assembly procedures. Assembly of the cell prior to use and disassembly after use are both time consuming and prone to human error, raising the possibility of improper assembly and leakage, failed experiments and the resulting loss of valuable time, and the potential loss of samples.

SUMMARY OF THE INVENTION

This invention resides in a vertical slab gel electrophoresis apparatus that can be assembled in very few steps, while still achieving precise alignment of the gels with other parts of the apparatus, full contact of the exposed upper and lower edges of the gels with the appropriate electrode buffers, and secure sealing against leakage between the buffers. By a single motion, parallel plate gel enclosures or cassettes are clamped against a frame that serves as a rack both to hold the enclosures in position and to seal the enclosures to the walls and base of the frame in a liquid-tight manner. The seal forms a liquid-retaining chamber which is in fluid communication with the upper edges of the gel enclosures. A similar single motion releases the gel enclosures from the frame so that the gels are quickly removed after use for analysis. The frame includes exposed electrodes wired to plugs accessible for power connections. One electrode resides within the chamber formed by the combined frame and gel enclosures, which permits this electrode to serve as the upper electrode for the gels when a buffer solution is placed within the chamber. The other electrode resides outside the chamber so that it can serve as the lower electrode when the combined frame and gel enclosures are placed in a tank containing a second buffer solution.

The clamping function is achieved by a movable pressure plate whose movement is controlled by a pair of cams, the pressure plate and cams contained in a second frame or housing. The gel enclosures and frame referred to in the preceding paragraph are placed inside this second frame in contact with the pressure plate. The frame clamped directly to the gel enclosures may thus be referred to as an "inner frame" while the frame containing the pressure plate and cams may be referred to as an "outer frame" or "clamping frame." The cams are designed for manual rotation, and the cams and pressure plate together assert a uniform clamping pressure on the inner frame and gel enclosures. A single pressure plate and pair of cams serve to seal two gel enclosures against the inner frame. The outer or clamping frame is further designed to permit full access to the lower electrode when the inner frame and gel enclosures are clamped inside and the combination is placed in the tank of buffer solution.

Sealing of the gel enclosures to the inner frame is further enhanced by the use of a U-shaped gasket with a unique profile, flat on one side facing the inner frame and tapered on the other side facing the gel enclosure plates. Still further features, embodiments and advantages of the invention will be apparent from the description that follows.

BRIEF DESCRIPTION OF THE DRAWINGS

FIGS. 5a and 5b are from and side views, respectively, of the gasket component of the cell of FIG. 1. FIG. 5c is a cross section taken along the line C—C of FIG. 5a.

DETAILED DESCRIPTION OF THE INVENTION AND PREFERRED EMBODIMENTS

While the invention is susceptible of a wide range of constructions and implementations of its governing concepts, these concepts will best be understood by a detailed examination of a specific embodiment. One such embodiment is shown in the drawings.

Figure 1:
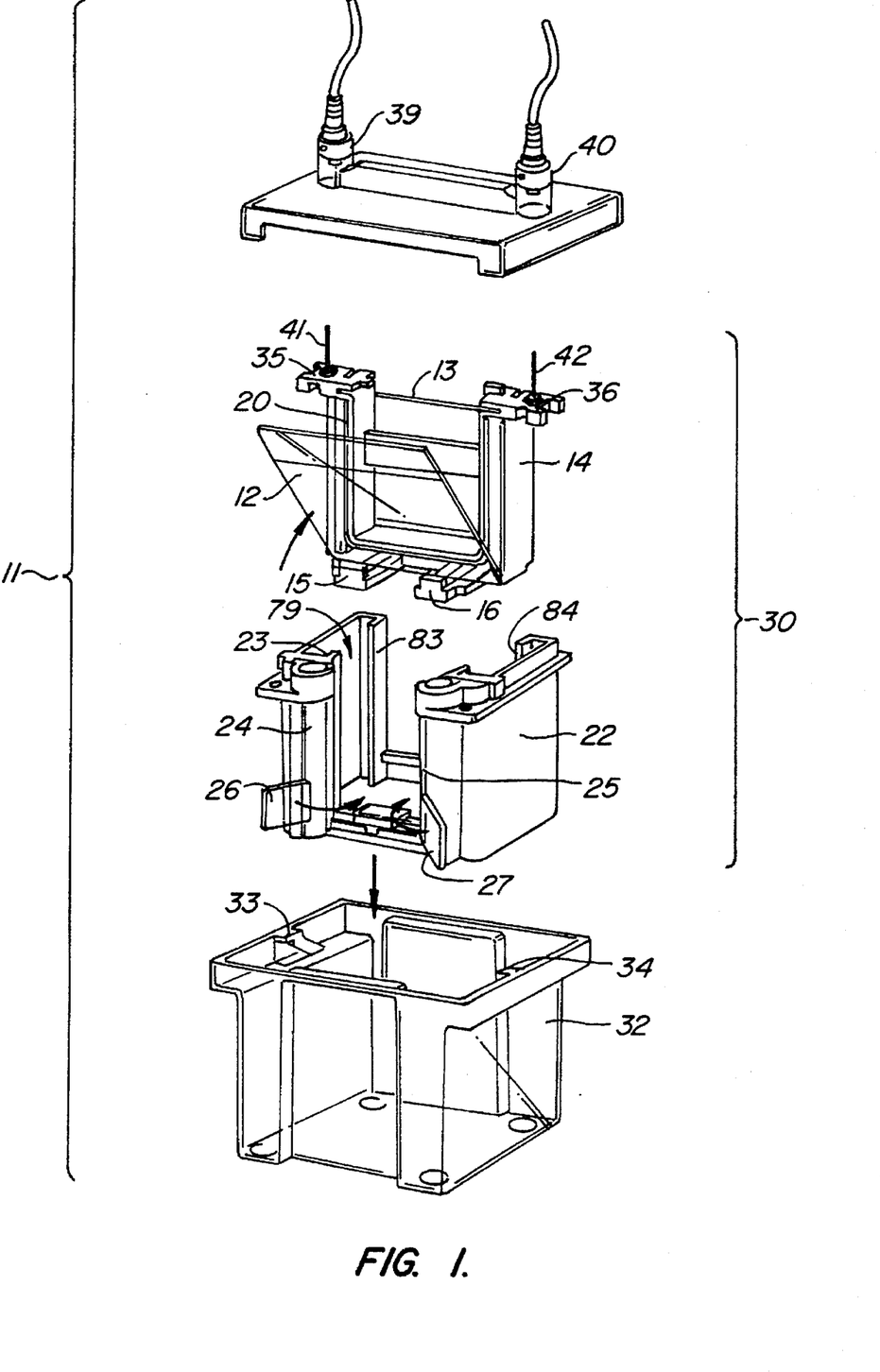
FIG. 1 is an exploded view in perspective of an electrophoresis cell with components incorporating the features of the present invention.

The component parts of a complete electrophoresis cell 11 are shown in FIG. 1. Two parallel plate gel enclosures 12, 13 are shown, positioned on either of two opposing faces of an inner frame or rack 14, the two gel enclosures and inner frame combining to form a liquid receptacle which will serve as the upper buffer chamber. Each gel enclosure consists of two flat plates of unequal height, separated by thin spacers along the two lateral sides of the plates, leaving a gap between the plates that defines the thickness of the gel. The two plates are positioned such that the bottom and side edges of both are aligned, with the top edge of the outer plate extending a short distance above the top edge of the inner plate. The shorter plates of both gel enclosures thus face the interior of the inner frame 14, with the taller plates on the outside and serving as retaining walls for the buffer solution whose liquid level is intermediate in height between the shorter and taller plates.

While the cell is shown with two gel enclosures, one forming each of the two broad faces of the upper buffer chamber, the cell can also be used with only a single gel by replacing one of the gel enclosures with a dam having generally the same exterior shape as the gel enclosure but solid in construction with neither a gel nor a gap, thereby preventing any fluid communication between the upper and lower buffer solutions.

Returning to the depiction of two gel enclosures as shown in the Figure, the forward gel enclosure 12 rests on grooved tabs 15, 16 extending from the bottom of the frame 14. The grooves in these tabs permit the enclosure to rotate away from the frame and also provide a convenient means for placing the enclosure against the frame in its proper position prior to clamping. In the drawing, the forward gel enclosure 12 is shown being rotated into position after its bottom edge has been placed in the grooves of the tabs. A U-shaped gasket 20 rests in a further groove considerably greater in length and extending along the front face of the frame. The U-shaped gasket seals the bottom edge and both sides of the gel enclosure. Although not visible in this drawing, the gasket has a stepped profile, i.e., an inverted shoulder facing the gel enclosure directly across from the top edge of the shorter plate, thereby sealing the gel enclosure to its full height. An identical gasket (not visible in this drawing) rests in a corresponding groove (also not visible) along the rear face of the frame, the two gaskets facing in opposite directions.

The outer or clamping frame 22 is shown below the gel enclosures 12, 13 and the inner frame 14. Retained inside the clamping frame 22 are the pressure plate 23 and the two cams 24, 25. Extending from each cam is a lever 26, 27 permitting rotation of the cam by hand. The arrows show the direction of rotation.

The gel enclosures 12, 13, inner frame 14 and outer frame 22 together form the inner chamber 30 of the electrophoresis cell, the chamber containing the gels and the upper buffer solution. Once assembled, the inner chamber 30 is inserted in a tank 32 which contains the lower buffer solution. Guides 33, 34 on the internal wall of the tank mate with projections 35, 36 on the inner frame to ensure proper and stable placement of the inner chamber inside the tank. The tank 32 is closed by a lid 38 which contains two female plugs 39, 40 to receive two banana plug jacks 41, 42 extending upward from the inner frame 14. Electric power is supplied to the cell through these connections.

Figure 2A:
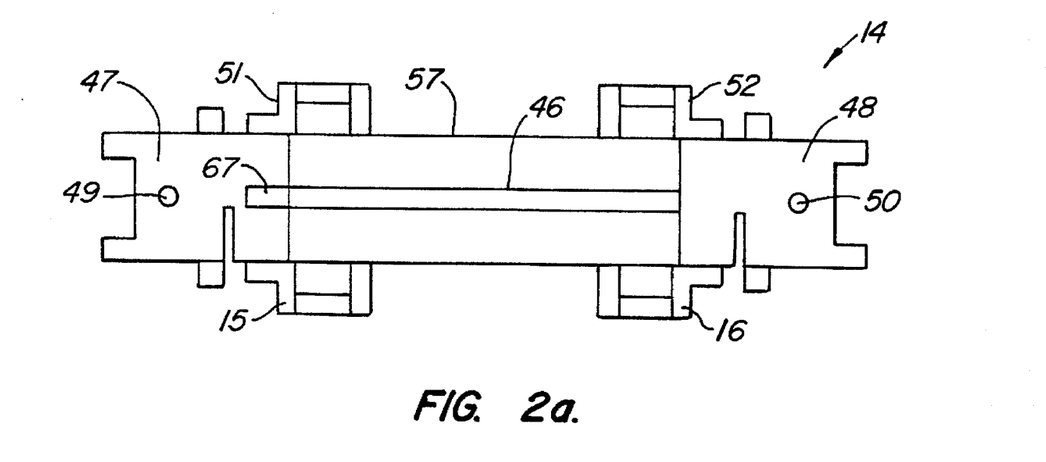
FIGS. 2a and 2b are top and front views, respectively, of the inner frame or rack component of the cell of FIG. 1, which when combined with two gel enclosures forms an upper buffer chamber.
Figure 2B:
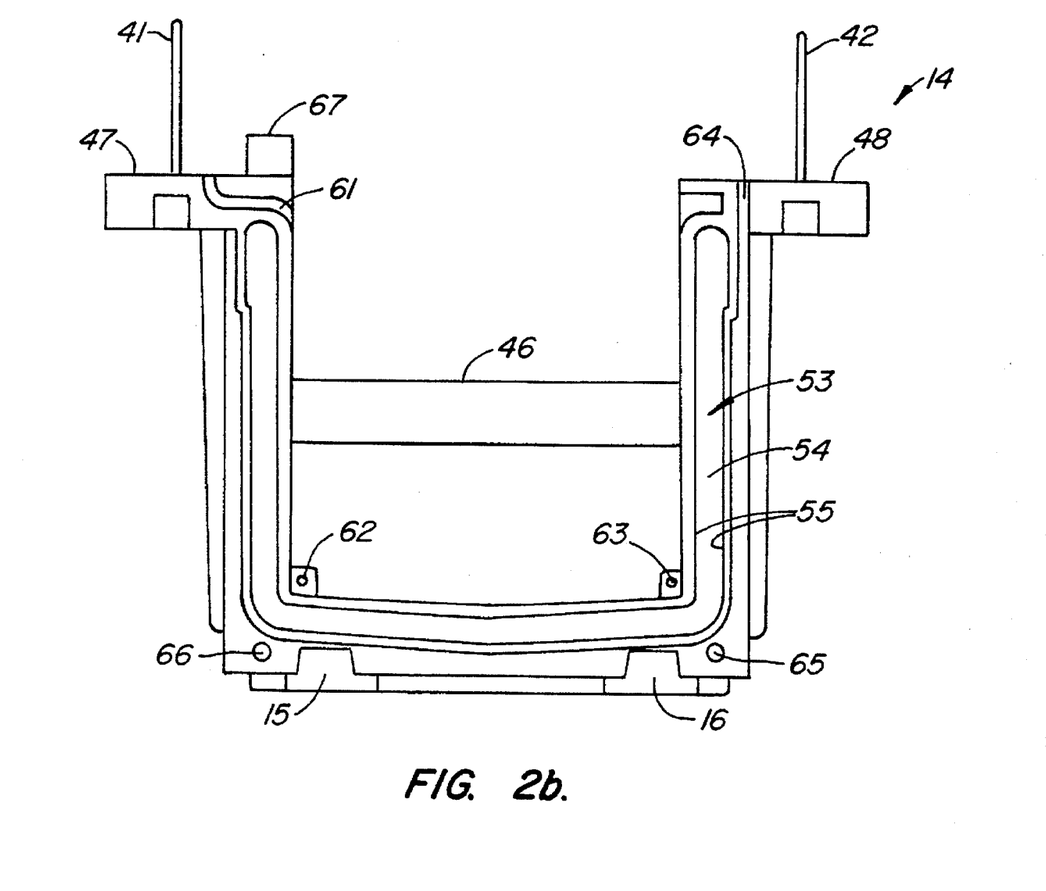

The inner frame 14 is shown in FIGS. 2a and 2b, in top and front views, respectively. Looking at these Figures together, the frame is generally U-shaped, with a crossbar 46 for structural reinforcement. The frame contains two side arms 47, 48 that rest on the upper edge of the outer frame 22 (FIG. 1). Holes 49, 50 are present in the side arms to receive the banana plug jacks. The holes are shown in FIG. 2a. The banana plug jacks themselves 41, 42 are shown in FIG. 2b. The grooved tabs 15, 16 extending from the bottom of the frame on one side to support the lower edge of the gel enclosure are matched by identical tabs 51, 52 on the opposite side for the second gel enclosure. The gasket groove 53 in FIG. 2b is shown without the gasket. The floor 54 of the groove is flat and planar, bordered on either side by side walls 55. An identical groove (not visible in these Figures) exists on the rear face 57 of the inner frame to accommodate an identical gasket.

Passages and mounts for the electrodes are shown in FIG. 2b as follows. The wiring for the electrode for the upper buffer solution extends from the base of the banana plug jack 41 at the upper left of the figure through a passage 61 leading into the interior of the "U" of the gasket and thus into the receptacle that will contain the upper buffer solution. The wiring continues down to the base of the "U" where it passes through a mounting hole 62 and extends across the width of the "U" to a second mounting hole 63 on the opposite side. The wiring is preferably insulated for its entire length except for the portion extending between the two mounting holes 62, 63. Wiring for the electrode for the lower buffer solution extends from the base of the banana plug jack 42 at the upper right of the figure through a passage 64 that is entirely outside the "U" of the gasket. The wiring passes through two mounting holes 65, 66 at the bottom of the frame, and the exposed portion of the wire is between these two holes. Numerous other open passages and indentations appearing in FIGS. 2a and 2b are included for the purpose of maintaining a lightweight structure and reducing the amount and thereby the cost of material used in its construction.

A further feature of the inner frame is an orientation lug 67 protruding upward from the frame on one side. The purpose of this lug is to permit the lid 38 (FIG. 1) to be secured to the remainder of the cell in one orientation only, so that the banana plug jacks 41, 42 on the inner frame are coupled with the correct electrical connectors 39, 40 in the lid and hence the correct leads of the power supply to achieve a current flow in the desired direction for electrophoresis to take place in the gels. When an improper orientation is attempted, the lug 67 abuts a protrusion on the under surface of the lid or some other obstacle preventing the lid from being fully lowered into place.

Figure 3A:
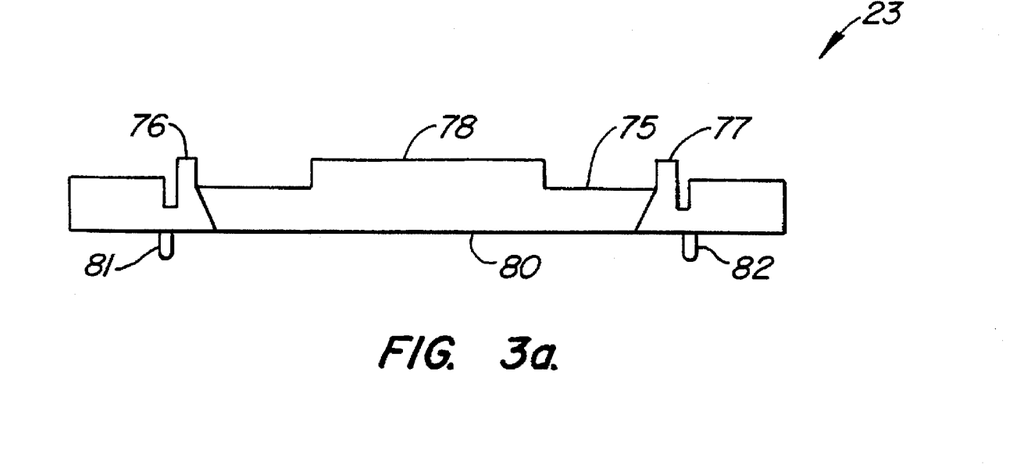
FIGS. 3a and 3b are top and front views, respectively, of the pressure plate component of the cell of FIG. 1.
Figure 3B:
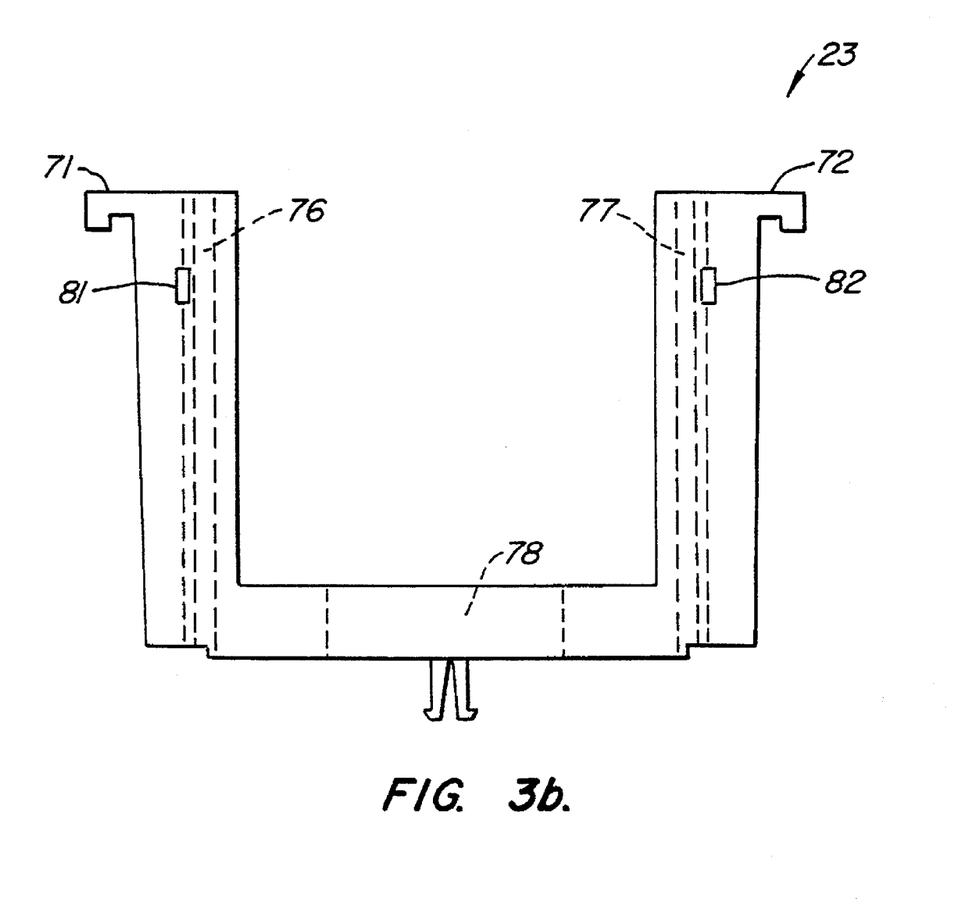

The pressure plate 23 is shown in FIGS. 3a and 3b, in top and front views, respectively. The pressure plate is also a U-shaped structure, with side arms 71, 72 to engage the upper edge of the clamping frame 22 (FIG. 1). A pair of hooks 73 at the base of the plate pass through and engage a hole in the base of the clamping frame (the hole is visible in FIG. 6a discussed below).

The side of the pressure plate facing the gel enclosure is the back side 75, indicated in FIG. 3a. A pair of raised ridges 76, 77 protrudes backward from the pressure plate, each ridge running vertically along the length of one of the two vertical sides of the "U" shape. These ridges are positioned to correspond to the locations of the two vertical portions of the gasket. As a result, the ridges will directly face the gasket through the plates of the gel enclosure. The back face of the pressure plate also contains a raised section 78 on the bottom of the "U" shape of the plate. This section is coplanar with the raised ridges 76, 77, and faces a portion of the gasket at the bottom of the "U" shape of the gasket. Thus, the raised ridges 76, 77 on the sides of the pressure plate and the raised section 78 on the base provide the regions of contact with the gel enclosure. The space between the back 75 of the pressure plate and the rear of the clamping frame provide a cavity 79 (indicated in FIG. 1) to receive the gel enclosures and inner frame.

The cams contact the front side 80 of the pressure plate, forcing the plate backwards into the cavity. A pair of lugs 81, 82 protruding from the forward side of the plate serve as stops for the cams, preventing the cams from rotating beyond the position at which they move the pressure plate the greatest distance backward. The lugs extend into notches in the cams (shown in FIG. 4b discussed below), and when the plate is secured to the clamping frame by the hooks 73, these lugs serve as retaining means for the cams, preventing the cams from falling out of the clamping frame when the frame is turned upside down for cleaning or other operations.

When the cams are in a clamping position, the pressure plate 23 thus compresses the cavity, forcing the gel enclosures and inner frame toward the back of the clamping frame 22, where the rear gel enclosure 13 (FIG. 1) meets a pair of inwardly protruding ridges 83, 84 (FIG. 1) inside the clamping frame. The gel enclosures and inner frame are thus clamped between these ridges and the pressure plate. In an alternative embodiment of the invention, the ridges 83, 84 are replaced by a second pressure plate and a second pair of cams, all operating identically to (and independently of) the first pressure plate and pair of cams. The gel enclosures and inner frame are thus clamped between two pressure plates. In preferred embodiments, however, a single pressure plate and pair of cams is present so that the clamping action need only be performed on one side of the clamping frame.

Figure 4A:
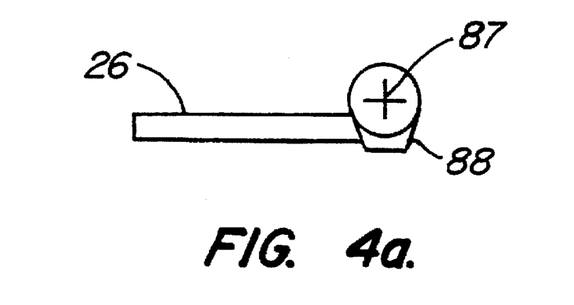
FIGS. 4a and 4b are top and side views, respectively, of the left cam component of the cell of FIG. 1.
Figure 4B:
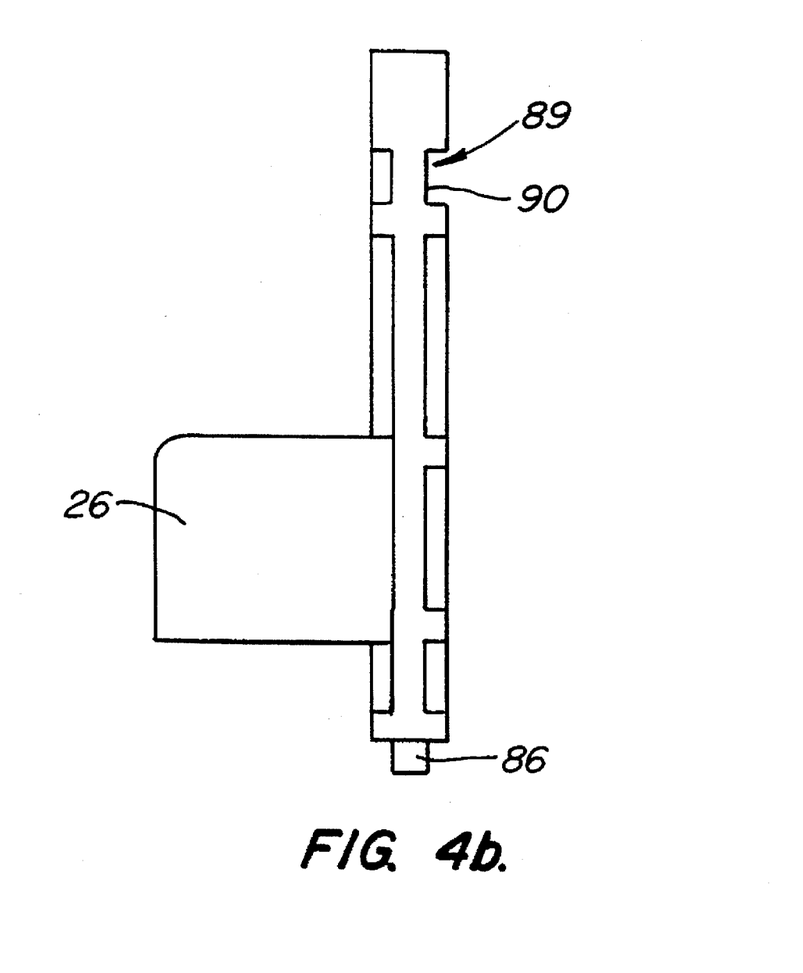

The left cam 24 is shown in FIGS. 4a and 4b, in top and side views, respectively. A pin 86 at the base of the cam (FIG. 4b) is received in a hole in the clamping frame. The cam rotates on an axis 87 (FIG. 4a), its rotation controlled by the lever 26. As the cam rotates, the eccentric portion 88 of the cam engages the pressure plate to force it backward, thereby achieving the clamping effect. The lug 81 on the pressure plate (FIGS. 3a and 3b) pass through a notch 89 on the cam shaft for a portion of the rotation of the shaft. Rotation is stopped when the lug engages the wall surface 90 inside the notch. As in other parts of the apparatus, the remaining indentations appearing in these figures are included for the purpose of maintaining a lightweight structure and reducing the cost of material used in the construction of the cam.

The right cam 25, although not shown separately in one of the Figures, is the mirror image of the left cam 24.

Figure 5A:
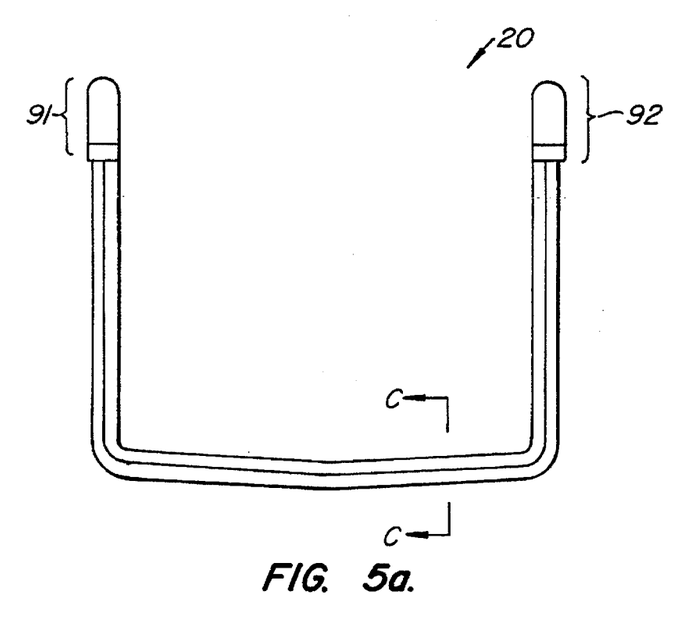
Figure 5B:
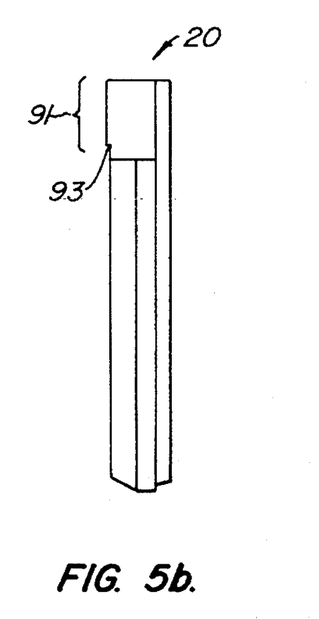
Figure 5C:
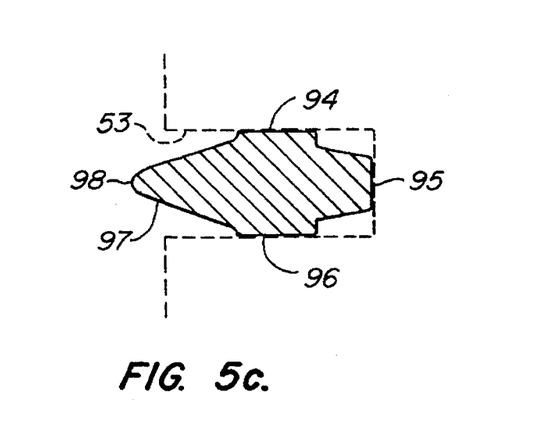

FIGS. 5a, 5b and 5c depict the gasket 20 in front view, side view and cross section, respectively, the cross section taken along the line C—C of FIG. 5a. As depicted in FIG. 5a, the front of the gasket is the surface contacting the gel enclosure plates. The two upper ends 91, 92 of the gasket are flat where the gasket contacts the gel plates. Each of these two ends has a stepped profile, however, as seen in FIG. 5b. The step 93 rests on the upper edge of the shorter plate of the gel enclosure. Thus, the flat surface below the step presses against the shorter plate while the flat surface above the step presses against the taller plate, thereby forming a full seal along the entire height of the gel enclosure. Alternative embodiments of the invention may be designed for gel cassettes with plates of equal rather than unequal height, and for these embodiments, the gasket will not have a stepped profile.

FIG. 5c shows the profile of the gasket together with the groove 53 in the face of the inner frame, the groove shown in dashed lines. The gasket surfaces 94, 95, 96 that are in contact with the groove walls are flat, particularly the surface 95 at the floor of the groove. The side 97 of the gasket facing the gel enclosure plates however is tapered, so that the contact between the gasket and the gel enclosure when the two are not forced together is a thin line 98. An advantage offered by this profile is that the tapered edge concentrates the sealing force along the smallest area of the gel enclosure, thereby minimizing the risk of distorting the gel. The flat surface on the opposite side provides a large sealing area against the inner frame where the surface is not as reliably smooth as the surface of the gel enclosure. A further advantage is that distortion of the gasket under pressure will cause a greater degree of spreading of the gasket material in the regions toward the floor of the groove. Also, minimizing the contact between the gasket and the gel enclosure makes it easier to disengage the gel enclosure from the gasket after contact under the heat typically generated in the gel during an electrophoresis procedure.

Figure 6A:
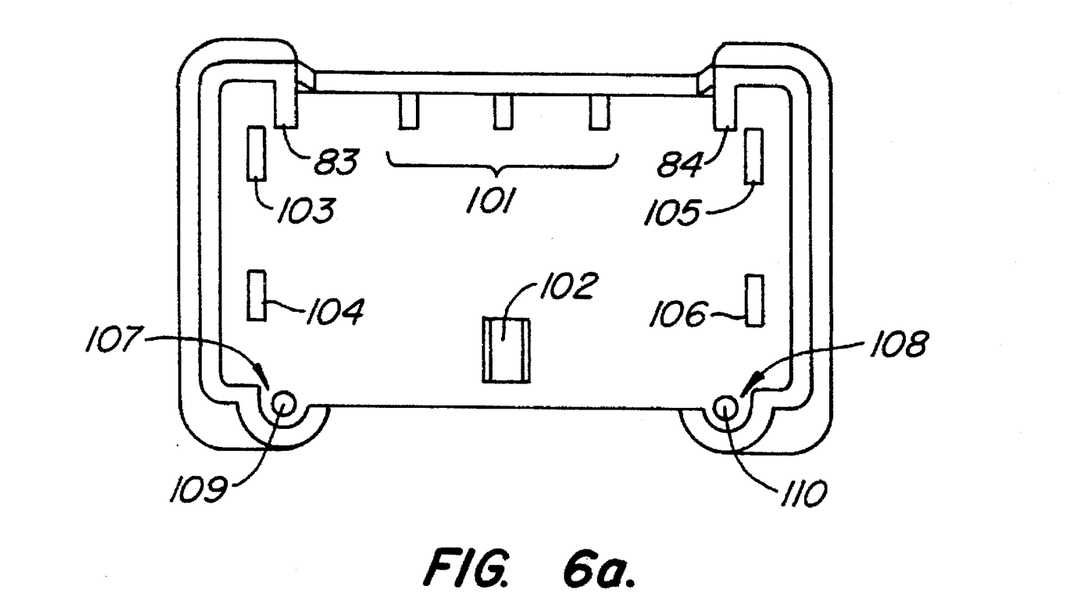
FIGS. 6a and 6b are top and front views, respectively, of the clamping frame component of FIG. 1.
Figure 6B:
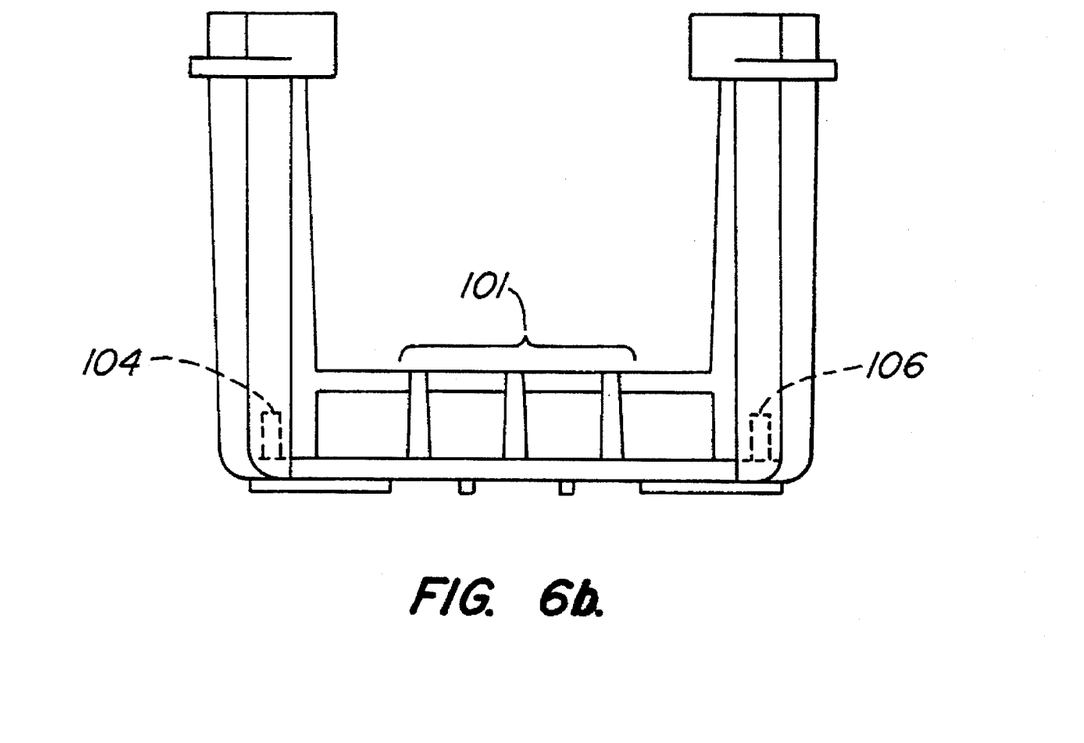

The clamping frame 2 without the pressure plate and the cams is shown in FIGS. 6a and 6b, which are top and front views, respectively. The inwardly protruding ridges 83, 84 are visible in the top view of FIG. 6a, and additional but shorter retaining ribs 101 are also shown. These shorter ribs are located along the bottom of the frame, and their inward edges are coplanar with the inward edges of the longer ridges 83, 84. The lower edges of the gel enclosures and inner frame are thus pressed between the shorter ribs 101 and the horizontal raised section 78 at the lower back of the pressure plate (FIG. 3a), while the side edges are compressed between the longer ridges 83, 84 and the corresponding vertical ridges 76, 77 at the lower back of the pressure plate. FIG. 6a further shows the hole 102 in the floor of the clamping frame to receive the hooks 73 extending downward from the underside of the pressure plate (FIG. 3b). Also shown in FIG. 6a is a further set of ribs 103, 104, 105, 106 on the floor of the frame extending upward. Since the ribs are positioned to contact only the gel enclosures along their lower edges and not the inner frame, a further function of the ribs is to push the gel enclosures upward as the inner frame is being pushed down, forcing the upper edges of the shorter plates against the gasket step 93 to achieve a tighter seal. Inside the frame and toward its forward face are curved recesses 107, 108 to receive the cam shafts and holes 109, 110 for the pins at the bottoms of the cam shafts (one such pin 86 is shown in FIG. 4b).

The cell is assembled for use in an electrophoretic separation in two vertical slab gels as follows. The slab gels are pre-formed in gel cassettes consisting of the gels and their gel enclosures. The upper and lower edges of the gels are exposed, the upper edge defined as the edge where the tall plate of the enclosure extends above the short plate. The lower edges of the gel cassettes are placed in the grooved tabs 15, 16 and 51, 52, respectively, of the inner frame 14, with the short plates facing inward. The cassettes are pressed against the gaskets 20 which have previously been placed in the corresponding grooves 53 of the inner frame. The two cassettes and inner frame are then placed inside the clamping frame 22 while the cam levers 26, 27 are rotated outward (in the position shown in FIG. 1). To complete this step, the user presses down on the side arms 47, 48 of the inner frame with the user's index fingers, while closing the two cam levers in the directions shown by the arrows in FIG. 1. The clamping frame with the gel cassettes and inner frame thus secured inside is then lowered into the tank 32. The chamber inside the inner frame is then filled with running buffer to a level between the tops of the short and tall plates of the cassettes, and further buffer is placed in the tank. The lid 38 is then placed over the tank with the banana plug jacks fully engaged by the electrical connections in the lid, and the cell is ready for the application of a current and the resulting electrophoretic separations.

The foregoing is offered primarily for purposes of illustration. It will be readily apparent to those skilled in the art that the configurations, relative dimensions, operating procedures and other parameters of this invention can be further modified or substituted in various ways without departing from the spirit and scope of the invention.

I claim:

1. Apparatus for securing a parallel plate gel enclosure to a frame to form a liquid-retaining chamber for an electrophoresis buffer, said apparatus comprising:

a gasket between said frame and said gel enclosure;

a housing;

a pressure plate movably received inside said housing, said pressure plate defining a cavity within said housing to receive said gel enclosure and frame;

a pair of cams rotatably mounted to said housing in engagement with said pressure plate; and means for rotating said cams to urge said pressure plate toward said cavity, such that when said gel enclosure, gasket and frame are received in said cavity, said gel enclosure is pressed against said gasket and frame to form a fluid-tight seal.

2. Apparatus in accordance with claim 1 in which said cams are parallel rods with cam-shaped profiles, positioned along opposing edges of, and extending the full length of, said gel enclosure.

3. Apparatus in accordance with claim 2 in which said means for rotating said cams are levers extending laterally from said parallel rods, and said rods are arranged to clamp against said pressure plate upon rotation of said levers in opposite directions.

4. Apparatus in accordance with claim 3 in which said levers are arranged to move said rods into a clamping position when said levers are parallel to said gel enclosure.

5. Apparatus in accordance with claim 1 in which said housing comprises two opposing sides, a floor, and means for maintaining a gap between said gel enclosure and frame and said floor.

6. Apparatus in accordance with claim 1 in which said gel enclosure is in the shape of a rectangle, and said gasket is substantially U-shaped and sized to extend along three sides of said rectangle, thereby sealing said gel enclosure against said frame along three edges of said gel enclosure.

7. Apparatus in accordance with claim 6 further comprising a U-shaped groove in said frame to receive said gasket.

8. Apparatus in accordance with claim 7 in which said groove is defined by a floor and side walls, said floor being flat and planar.

9. Apparatus in accordance with claim 8 in which said gasket has a flat side and a tapered side opposite said flat side, such that when said gasket, frame and gel enclosure are assembled, said flat side contacts said floor of said groove and said tapered side contacts said gel enclosure.

10. Apparatus in accordance with claim 1 in which said gasket is defined as a first gasket, said apparatus further comprises a second gasket, and said frame comprises first and second faces with grooves on each face to receive one of said gaskets, said apparatus thereby capable of receiving two gel enclosures, one on each side of said frame.

* * * * *